United States Patent [19]

Mazur

[11] Patent Number: 5,106,967
[45] Date of Patent: Apr. 21, 1992

[54] FUNCTIONAL SUGAR SUBSTITUTES WITH REDUCED CALORIES

[75] Inventor: Adam W. Mazur, Cincinnati, Ohio

[73] Assignee: The Procter & Gamble Company, Cincinnati, Ohio

[21] Appl. No.: 706,445

[22] Filed: May 28, 1991

Related U.S. Application Data

[60] Division of Ser. No. 653,333, Feb. 11, 1991, Pat. No. 5,041,541, which is a division of Ser. No. 339,531, Apr. 20, 1989, Pat. No. 5,064,672, which is a continuation-in-part of Ser. No. 190,486, May 5, 1988, abandoned.

[51] Int. Cl.$^5$ .................. C07H 3/06; C07H 13/02; C07H 15/04
[52] U.S. Cl. .................. 536/119; 536/1.1; 536/4.1; 536/115; 536/120
[58] Field of Search .............. 536/1.1, 4.1, 115, 120, 536/119

[56] References Cited

U.S. PATENT DOCUMENTS

| | | | |
|---|---|---|---|
| 2,876,105 | 3/1959 | Jucaitis et al. | 426/548 |
| 2,900,268 | 8/1959 | Rankin et al. | 536/1.1 |
| 3,356,674 | 12/1967 | Ikeda et al. | 536/1.1 |
| 3,600,186 | 8/1971 | Mattson et al. | 426/658 |
| 3,704,138 | 11/1972 | LaVia et al. | 426/548 |
| 3,893,996 | 7/1975 | Hamuro et al. | 536/1.1 |
| 3,954,976 | 5/1976 | Mattson et al. | 514/23 |
| 3,963,699 | 6/1976 | Rizzi et al. | 536/119 |
| 4,005,195 | 1/1977 | Jandacek | 514/23 |
| 4,005,196 | 1/1977 | Jandacek | 514/23 |
| 4,207,413 | 6/1980 | Szarek et al. | 536/1.1 |
| 4,262,032 | 4/1981 | Levin | 426/658 |
| 4,382,924 | 5/1983 | Berling et al. | 514/23 |
| 4,459,316 | 7/1984 | Bakal | 426/658 |
| 4,518,581 | 5/1985 | Miyake et al. | 536/1.1 |
| 4,786,722 | 11/1988 | Zehner | 536/1.1 |
| 4,871,776 | 10/1989 | DiNovi et al. | 514/738 |
| 5,041,541 | 8/1991 | Mazur | 536/1.1 |

OTHER PUBLICATIONS

"The Sweetener Report, 1982–1987", Food Engineering, 54, No. 7, pp. 75–83, 85 1982.
Witzak and Whistler, Carbohydrate Research, 169, pp. 252–257, 1987.
Dziezak, Food Technology, pp. 112–128 (1986).
CRC, vol. 11, No. 4, pp. 401–413 (1979).
Paul and Palmer, Food Theory and Applications, p. 47 (1972).
Hedgley et al; Chemistry and Industry 938–939, Jul. 16, 1960.
Kirk and Othmer, Encyclopedia of Chemical Information 3rd. ed., vol. 21, pp. 939–943 (1978).
Youssefyeh, et al. 4'-Substituted Nucleosides.4.Synthesis of Some 4'-Hydroxymethyl Nucleosides, 1979, J. Org. Chem., vol. 44, pp. 1301–1309.

*Primary Examiner*—Johnnie R. Brown
*Assistant Examiner*—Nancy S. Carson
*Attorney, Agent, or Firm*—Rose Ann Dabek; Jerry J. Yetter; Richard C. Witte

[57] ABSTRACT

Disclosed are novel 5-C-hydroxymethylhexose compounds and their derivatives which exhibit sugar-like functionality when used in food compositions. The derivatives include stereoisomers, di-, tri-, and polysaccharides, alkyl glycosides, polyol, and alditol derivatives. Also disclosed are sugar substitute compositions and food compositions containing these compounds and their derivatives.

12 Claims, No Drawings

FUNCTIONAL SUGAR SUBSTITUTES WITH REDUCED CALORIES

This is a division of application Ser. No. 07/653,331, filed on Feb. 11, 1991, now U.S. Pat. No. 5,041,541, issued Aug. 20, 1991, which is a division of application Ser. No. 07/339,531, filed on Apr. 20, 1989, now U.S. Pat. No. 5,064,672, issued Nov. 12, 1991, which is a continuation-in-part of Ser. No. 190,486, filed May 5, 1988, now abandoned.

TECHNICAL FIELD

This invention relates to novel 5-C-hydroxymethyl hexose-based compounds and their use as sugar substitutes. These carbohydrates provide sugar-like functionality while having significantly reduced calories compared to sucrose. This invention also relates to food and beverage compositions which include these carbohydrates.

BACKGROUND OF THE INVENTION

The ready availability of a variety of highly flavorful foods coupled with the relatively sedentary lifestyles of a portion of the population has resulted in an accumulation of calories in these people. Estimates indicate that currently as much as 40% of the U.S. population is overweight. J. J. Beereboom, *CRC Critical Reviews in Food Science and Nutrition*, 11(4), pps. 401-413, May 1979. Consequently, an increasing number of people are practicing some form of dieting and/or monitoring of caloric intake. This has led to the successful introductions and rapid growth of a variety of reduced calorie food products, such as cake mixes, beers, wines, candies and sodas.

Two of the most significant contributors to the population's caloric intake are sucrose (i.e., common table sugar) and high fructose corn syrup. In fact, a great deal of effort has been expended to develop a functional reduced calorie sugar substitute.

In 1985, the Calorie Control Council's brochure *Sweet Choices* described the ideal sweetener as having the following characteristics:
  same or greater sweetness as sucrose
  colorless
  odorless
  readily soluble in water
  stable
  functionally similar to sucrose
  economically feasible
  contribute reduced or no calories to the diet
  non-toxic and non-promoting of dental caries
The Council commented that up to that date a sweetener having all those characteristics did not exist.

Sugars are best known as sweeteners, however, their role as functional components in foods is equally important. Sugar influences many food properties in addition to flavor. It alters the degree of hydration of many substances, influences the viscosity of starch pastes, the firmness of gelatin and pectin gels, and the formation and strength of gluten strands. It controls the gelatinization temperature of starch and the gelation temperatures of gluten and egg proteins. It affects the rate of spoilage due to the growth of micro-organisms. In many cases, it alters the color and texture of fruit products. It increases the moisture-retaining ability of many foods. The size of sugar crystals influences markedly the textural characteristics of candies and frostings, and it enhances the body of beverages. (See Paul and Palmer, *Food Theory and Applications*, pg. 47 (1972)). The concentration of sugar in the food product regulates the properties. As a result, the volume fraction of sugar in foods is often very high. This is commonly referred to as sugar's bulking characteristic. One of the major problems in developing a reduced calorie sugar substitute is to provide this bulking characteristic.

Most artificial sweeteners in use today have a greater relative sweetness than sucrose; thus, relatively small quantities are required to deliver the desired sweetness. Such low volume sweeteners may be acceptable for certain applications (e.g., beverages), however, they do not provide sufficient bulk and functionality for use in solid and semi-solid foods like baked goods and frozen desserts. In fact, even high intensity sweetener-containing beverages have a detectable reduction in their body. Two avenues have been explored to overcome this bulking problem:
  combinations of bulk extenders and available artificial sweeteners
  modified sugars Presently-available sweeteners and sweetener/bulk extender combinations are not satisfactory due to their significant deviation from the important functional characteristics of sucrose (e.g., solubility and control of starch gelatinization), significant caloric values, and negative physiological effects.

Polydextrose, produced by Pfizer Corp., is a non-sweet, randomly bonded glucan containing small amounts of sorbitol and citric acid. It is presently the most widely used reduced calorie bulk extender in foods. As a sugar substitute it contributes 1 kcal/g, which is equivalent to about 25% of the caloric contribution of sucrose. Unfortunately, polydextrose has a low laxative threshold and has little control of starch gelatinization. See Food Technology, January 1986, "Special Report: Sweeteners and Product Development", pg. 129.

U.S. Pat. No. 2,876,105, Jucaitis and Biudzius, issued Mar. 3, 1959, discloses another class of carbohydrate polymers to be used as bulk extenders. Other bulk extenders include gum arabic and gum tragacanth. However, they are not desirable since they are not readily soluble, especially in cold liquids, and they have high relative viscosities and they have little control of starch gelatinization. See U.S. Pat. No. 3,704,138, LaVia, issued Nov. 28, 1972.

Arabinogalactan (Larch Gum) is a highly branched polymer of arabinose and galactose obtained from the Western Larch tree. Though it has FDA clearance for use in foods and has many suitable physical properties, such as good solubility in solutions having low viscosities, actual use has been small due to taste, functional, heat-stability problems and poor starch gelatinization control.

U.S. Pat. No. 4,207,413, Szarek et al., issued June 10, 1980, discloses that L-sucrose ($\alpha$-L-glucopyranosyl-$\beta$-L-fructofuranoside) has identical sweetness to sucrose but is not metabolized on ingestion and is, therefore, non-caloric. The high cost of synthesizing this compound acts as a significant barrier to its development as a dietary sweetening agent. See Kirk-Othmer, *Encyclopedia of Chemical Technology*, third ed., Vol. 21, pg. 939 (1978). A later patent discloses that L-monosaccharides are also edible and non-caloric (U.S. Pat. No. 4,262,032, Levin, issued Apr. 14, 1981). These L-sugars are also very costly to synthesize.

Sugar alcohols, called alditols, have also been proposed as sugar substitutes. However, only a few alditols have been approved as food additives and they have limited dietary applications due to their low laxative threshold and significant caloric value. (See, Rothschild, *Food Chemical News Guide*, mannitol, pg. 255 (1987); sorbitol, pg. 430 (1982); xylitol, pg. 495 (1986)).

In order to test structure-sweetness correlations, Witczak and Whistler, Carbohydrate Research, 169 (1987), 252-257, synthesized a large group of compounds including the branched chain alditol, 2-C-(hydroxymethyl)-D-mannitol. Witczak and Whistler did not comment on the metabolizability of the compound.

U.S. Pat. No. 4,459,316, Bakal, issued July 10, 1984, teaches that di- and trisaccharides containing one levohexose component and at least one dextrohexose component (e.g., $\alpha$-L-glucopyranosyl-D-fructofuranose) are non-caloric. These disaccharides are costly to synthesize due to the fact that they are prepared from a racemic mixture of D-hexoses and expensive L-hexoses.

Thus, a sugar replacement which is low in calories, inexpensive to synthesize, sweet, functional (especially as a bulking agent) and avoids negative physiological effects is highly desirable.

It has now been found, that carbohydrates in the 5-C-hydroxymethyl-hexose series can be effectively used as replacements for sugar, especially in baked goods. These carbohydrate derivatives provide sucrose-like functionality (i.e., bulk, texture and stability) with significantly reduced calories compared with sucrose. In addition, many of these carbohydrate derivatives are easier to synthesize than currently available functional sugar substitutes. It is believed that they are essentially free of the significant negative physiological effects (i.e., flatus and diarrhea) generally associated with such compounds. It has also been shown that saccharides containing a 5-C-hydroxymethyl-hexose component provide similar benefits. This also holds true for the alditols of these carbohydrates (e.g., 5-C-hydroxymethyl-hexitols, 5-C-hydroxymethyl-aldohexosyl polyol derivatives, alkyl derivatives (e.g., 5-C-hydroxymethyl-aldohexosyl glycerol and 5-C-hydroxymethyl-aldohexosyl-glucitol) of the carbohydrates (i.e., alkyl 5-C-hydroxymethyl-aldohexosides), and 1,6-anhydro-$\beta$-L-, and 1,6-anhydro-$\beta$-D derivatives of the pyranose compounds (i.e., the bicyclic tautomeric forms) and the related derivatives of the ketohexoses.

SUMMARY OF THE INVENTION

The novel carbohydrates of the present invention encompass 5-C-hydroxymethyl-hexose monosaccharides, and several specific derivatives. The carbohydrates include 5-C-hydroxymethyl derivatives of allose, -altrose, -glucose, -mannose, -gulose, -idose, -galactose, -talose, -fructose, -psicose, -sorbose and -tagatose in their D or L configuration and as the $\alpha$ or $\beta$ anomer. These carbohydrates include the straight-chain, pyranose and furanose tautomeric forms. The specific novel derivatives of 5-C-hydroxymethyl-aldohexose include 1,6-anhydro-$\beta$-L-aldohexoses, 1,6-anhydro-$\beta$-D-aldohexoses, alkyl 5-C-hydroxymethyl-aldohexosides and polyols derived from 5-C-hydroxymethyl-aldohexosyl compounds. Also included are alkyl 5-C-hydroxymethyl-ketohexosides and polyols derived from 5-C-hydroxymethyl-ketohexosyl compounds.

The invention also comprises novel di-, tri-, oligo- and polysaccharides containing at least one simple sugar linkage from the above-mentioned novel carbohydrates.

The invention also encompasses sugar substitute compositions, providing nearly identical sweetness and bulk when compared to sucrose, which comprise the novel carbohydrates or their alditols blended with conventional artificial sweeteners or with mixtures of conventional sugars and artificial sweeteners, and, optionally conventional bulking agents.

The invention further encompasses food compositions (e.g., beverages, baked goods, frozen deserts and candies) containing the above-mentioned novel carbohydrates or their alditols.

Other novel food compositions of the present invention include fat-containing foods containing the above-mentioned carbohydrates or their alditols in combination with polyol polyesters.

DETAILED DESCRIPTION OF THE INVENTION

All ratios and percents described herein are "by weight" unless otherwise specified.

DEFINITIONS

The term "baked goods" refers to all manner of foods which are cooked (i.e., prepared using heat). These baked goods include, but are not limited to, foods prepared using dry heat (i.e., a radiant or convection oven), fried foods, boiled foods and foods heated in a microwave oven.

The term "food compositions" refers to and includes all manner of viand (both sweetened and un-sweetened foods) for usage by man or animal. These food stuffs include, but are not limited to, baked goods, salted snacks, other flavored snacks, fruit drinks/mixes, frozen foods, candies, carbonated beverages, milk drinks/mixes, gelatins, puddings, fillings, breakfast cereals, breakfast bars, sauces, jams, jellies, whipped toppings, tablets, syrups, orally administered medicines, spreads, chewing gums and chocolates.

The term "galactose oxidase" as used herein refers to D-galactose: oxygen 6-oxidoreductase which is identified as E.C. 1.1.3.9 or as Chemical Abstracts Registry Number 9028-79-9.

The term "catalase", as used herein, refers to $H_2O_2$:-$H_2O_2$ oxidoreductase which is identified as E.C. 1.11.1.6. Catalase is an oxidizing enzyme which decomposes hydrogen peroxide. These enzymes occur in both plant and animal cells.

The term "bulking compound" as used herein refers to a compound which provides acceptable bulk (i.e., displacement) and similar functionality when compared with sucrose in food composition applications.

The term "sweetening compound" as used herein refers to a compound which produces a sweet sensory response. Sweetening compounds include, but are not limited to: sucrose, glucose, fructose, lactitol, maltitol, sorbitol, alitame, sucralose, acesulfame, aspartame, cyclamates, saccharin and mixtures of these compounds. The term "sweetening compound" does not refer to any of the novel compounds described herein or their alditols.

The term "sugar substitute" as used herein refers to a composition which is effective in replacing conventional sugars (i.e., sucrose, fructose, glucose, etc.) in food compositions and provides sugar-like functionality in the form of degree of hydration, viscosity, color, texture, odor, presentation and bulk, but with significantly reduced calories.

The term "hexose" means a carbohydrate containing six carbons. This term encompasses both aldehyde containing hexoses (aldohexoses) and ketone containing hexoses (ketohexoses).

The term "aldohexoses" refers to the group of sugars whose molecule contains six carbon atoms, one aldehyde group and five alcohol groups. The sixteen stereoisomers of the aldohexose series are D-allose, D-altrose, D-glucose, D-mannose, D-gulose, D-idose, D-galactose, D-talose, L-allose, L-altrose, L-glucose, L-mannose, L-gulose, L-idose, L-galactose and L-talose. These sugars exist in solution as an equilibrium mixture of several "tautomeric forms": a pyran-ring form; a furan-ring form; or a straight-chain aldehyde form. Tautomeric forms of D-glucose:

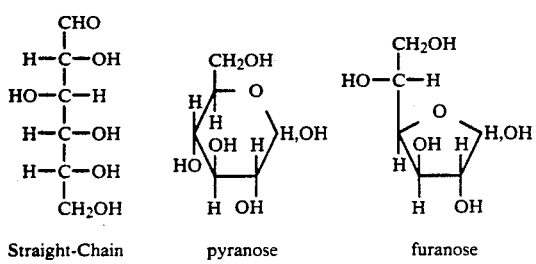

Straight-Chain    pyranose    furanose

Aldohexoses may also occur in an α or β anomeric configuration, depending on the position of the C-1 hydroxyl group. Examples are:

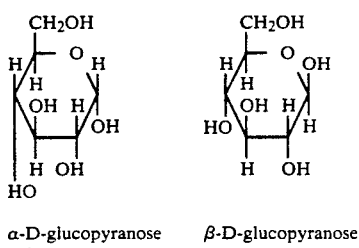

α-D-glucopyranose    β-D-glucopyranose

The term "D-ketohexose" refers to the group of sugars which contain six carbon atoms, one ketone group and five alcohol groups. The eight stereoisomers are D- and L- isomers of psicose, fructose, sorbose and tagatose. Like the aldohexoses, these ketohexoses can exist in solution as an equilibrium mixture of several "tautomeric forms": pyran-ring; a furan ring and a straight chain ketone form.

The terms "sugar derivatives" and "novel compounds" as used herein refer to the 5-C-hydroxylmethyl derivatives of the hexose and their stereoisomers and polymers which are the subject of this invention.

The term "polyol polyester" refers to sugar fatty acid polyesters or sugar alcohol fatty acid polyesters having at least 4 fatty acid ester groups with each fatty acid having from 8 to 22 carbon atoms. Such polyesters and their use in conventional food products have been disclosed in, for example, U.S. Pat. No. 3,600,186, Mattson et al., issued Aug. 17, 1971; U.S. Pat. No. 3,954,976, Mattson et al., issued May 4, 1976; U.S. Pat. No. 3,963,699, Rizzi et al, issued June 15, 1976; U.S. Pat. No. 4,005,195, Jandacek, issued Jan. 25, 1977; U.S. Pat. No. 4,005,196, Jandacek et al., issued Jan. 25, 1977; and U.S. Pat. No. 4,382,924, Berling et al., issued May 10, 1983.

The term "polyol" includes all polyhydric alcohols (i.e., those compounds of the general formula $CH_2OH(CHOH)_nCH_2OH$, where n may be from 0 to 5.) glycerol contains three hydroxyl groups. Those with more than three are called sugar alcohols.

DESCRIPTION OF THE NOVEL COMPOUNDS

The novel 5-C-hydroxymethylaldohexose monosaccharides of the present invention include the following:

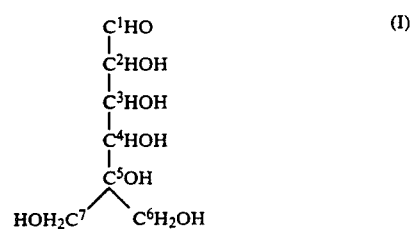

5-C-hydroxymethylaldohexose (straight-chain)

The preferred embodiments of the straight-chain 5-C-hydroxymethylaldohexose compounds are 5-C-hydroxymethyl derivatives of galactose, glucose, and mannose. Due to the relative ease of synthesizing galactose-based compounds, 5-C-hydroxymethyl derivatives of D-galactose is the most preferred compound.

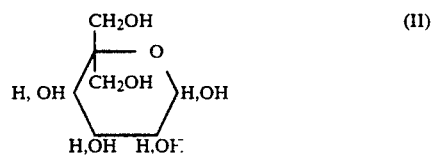

5-C-hydroxymethylaldohexopyranose

The preferred embodiments of the 5-C-hydroxymethylaldohexopyranose compounds are 5-C-hydroxymethyl derivatives of galactopyranose, -glucopyranose, and -mannopyranose. Due to the relative ease of synthesizing galactose-based compounds, 5-C-hydroxymethyl derivative of D-galactopyranose is the most preferred compound.

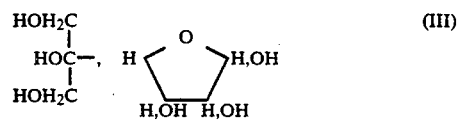

5-C-hydroxymethylaldohexofuranose

The preferred embodiments of the 5-C-hydroxymethylaldohexofuranose compounds are 5-C-hydroxymethyl derivatives of galactofuranose, -glucofuranose, and -mannofuranose. Due to the relative ease of synthesizing galactose-based compounds, 5-C-hydroxymethyl derivative of D-galactofuranose is the most preferred embodiment.

The novel 5-C-hydroxymethyl-aldohexose derivatives of this invention include:

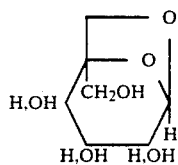

(IV)

1,6-anhydro-5-C-hydroxymethyl-β-D-aldohexopyranose

The preferred embodiment of the 1,6-anhydro-5-C-hydroxymethyl-β-D-aldohexopyranose compounds is 1,6-anhydro-5-C-hydroxymethyl-β-D-galactopyranose.

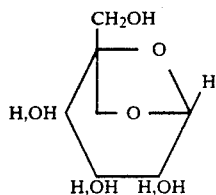

(V)

1,6-anhydro-5-C-hydroxymethyl-β-L-aldohexopyranose

The preferred embodiments of the 1,6-anhydro-5-C-hydroxymethyl-β-L-aldohexopyranose compounds are 1,6-anhydro-5-C-hydroxymethyl-β-L-altropyranose, -gulopyranose and idopyranose. The most preferred embodiment is 1,6-anhydro-5-C-hydroxymethyl-β-L-altropyranose.

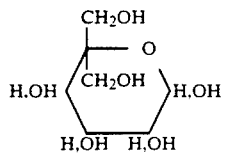

(VI)

Where R is an alkyl group containing one to four carbon atoms alkyl 5-C-hydroxymethyl-aldohexopyranoside The preferred embodiments of alkyl 5-C-hydroxymethylaldohexopyranosides are ethyl and methyl 5-C-hydroxymethylaldohexopyranoside. The most preferred embodiment is ethyl D-galactopyranoside.

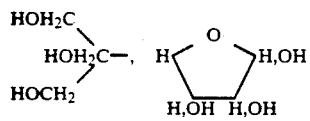

(VII)

Where R is an alkyl group containing one to four carbon atoms alkyl 5-C-hydroxymethylaldohexofuranoside The preferred embodiments of alkyl 5C-hydroxymethylaldohexofuranosides are ethyl and methyl 5-C-hydroxymethylaldohexofuranoside. The most preferred embodiment is ethyl 5-C-hydroxymethyl-L-arabinohexofuranoside.

(VIII) Another novel derivative of the present invention occurs when a polyol is covalently bound by a glycoside linkage to one of the above-mentioned 5-C-hydroxymethylated saccharides. Preferred embodiments of these compounds include:

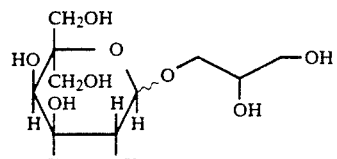

5-C-hydroxymethyl-α-L-arabino-hexopyranosyl-(1→1)-glycerol;

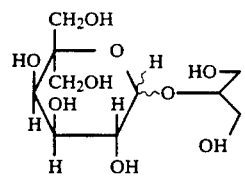

5-C-hydroxymethyl-β-L-arabino-hexopyranosyl-(1→2)-glycerol; and

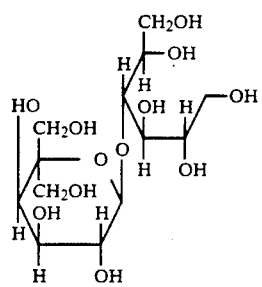

5-C-hydroxymethyl-α-L-arabino-hexopyranosyl-(1→4)-D-glucitol (a lactitol derivative).

Other monosaccharides based on the ketohexose derivatives are:

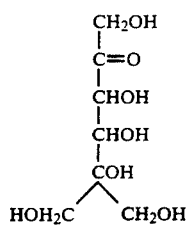

(IX)

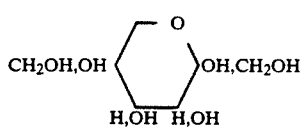

(Xa)

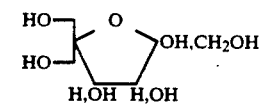

(Xb)

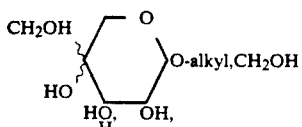

(XIa)

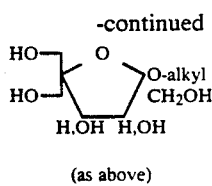

(as above)

Preferred embodiments are 5-C-hydroxymethyl derivatives of fructose and sorbose, including alkyl glycosides, due to the availability of natural sugars.

The monosaccharides discussed above (I–XI) may also be classified as simple sugars. Simple sugar linkages are the building blocks for di-, tri-, oligo- and polysaccharides. The novel di-, tri-, oligo- and polysaccharides of the present invention contain at least one simple sugar group (i.e., monosaccharides, monosaccharide derivatives) from the monosaccharides discussed above (I–XI) or their alditols covalently bound through glycoside linkages to one or more simple sugar or simple sugar groups through any of the glycoside acceptor carbon positions (i.e., C-1 through C-7). The preferred glycoside linkages are through (C-1 and C-4.

Preferred disaccharides comprise at least one simple sugar linkage selected from the group consisting of 5-C-hydroxymethylaldohexose; 1,6-anhydro-5-C-hydroxymethyl-β-D-aldohexopyranose; 1,6-anhydro-5-C-hydroxymethyl-β-L-aldohexopyranose; 5-C-hydroxymethylaldohexosyl polyol and alkyl 5-C-hydroxymethylaldohexoside, where the alkyl group is selected from the group consisting of methyl, ethyl, propyl and isopropyl.

Other preferred disaccharides comprise at least one simple sugar linkage selected from the group consisting of 5-C-hydroxymethylketohexose; 5-C-hydroxymethylketohexosyl polyol and alkyl 5-C-hydroxymethylketohexoside wherein the alkyl group is selected from the group of methyl, ethyl, propyl and isopropyl.

The following disaccharides are most preferred compounds:

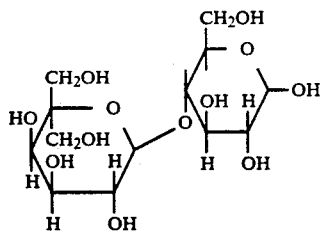

5-C-hydroxymethyl-α-L-arabino-hexopyranosyl-(1→4)-D-glucopyranose;

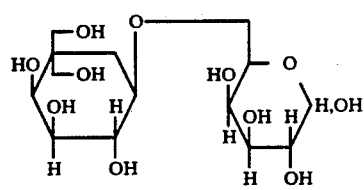

5-C-hydroxymethyl-α-L-arabino-hexopyranosyl-(1→6)-D-galactopyranose;

5-C-hydroxymethyl-α-L-arabino-hexopyranosyl-(1→6)-(α+β)-D-galactofuranose; and 5-C-hydroxymethyl-α-D-xylo-hexopyranosyl-β-D-fructofuranoside(a sucrose derivative).

The preferred disaccharides containing 5-C-hydroxymethyl keto hexoses are:

KETOHEXOSE DERIVATIVES DISACCHARIDES

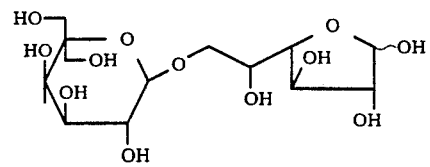

(A)
α-D-glucopyranosyl-5-C-hydroxymethyl-β-D-erythrohexulofuranoside (B)
5-C-hydroxymethyl-α-D-xylo-hexopyranosyl-5-C-hydroxymethyl-β-D-erythrohexulofuranoside The preferred trisaccharides comprise at least one simple sugar linkage selected from the group consisting of 5-C-hydroxymethylaldohexose; 1,6-anhydro-5-C-hydroxymethyl-β-D-aldohexopyranose; 1,6-anhydro-5-C-hydroxymethyl-β-L-aldohexopyranose; 5-C-hydroxymethylaldohexosyl polyol derivatives and alkyl 5-C-hydroxymethyl-D-aldohexoside, where the alkyl is selected from the group consisting of methyl, ethyl, propyl and isopropyl. The most preferred trisaccharide embodiment is:

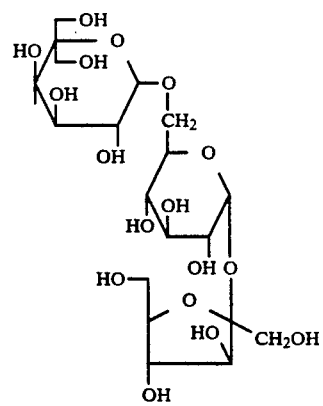

5-C-hydroxymethyl-β-L-arabino-hexopyranosyl-α-D-glucosyl-β-D-fructofurnoside (a raffinose derivative).

Preferred oligosaccharides comprise at least one simple sugar linkage selected from the group consisting of 5-C-hydroxymethylaldohexose; 1,6-anhydro-5-C-hydroxymethyl-β-D-aldohexopyranose; 1,6-anhydro-5-C-hydroxymethyl-β-L-aldohexopyranose; 5-C-hydroxymethylaldohexosyl polyol derivatives and alkyl 5-C-hydroxymethylaldohexoside, where the alkyl group is selected from the group consisting of methyl, ethyl, propyl and isopropyl.

The most preferred oligosaccharide embodiment is:

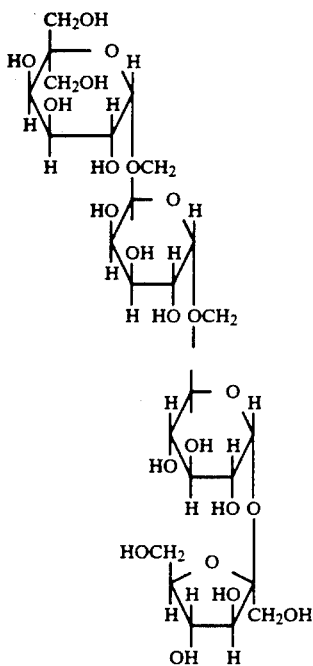

5-C-hydroxymethyl-α-D-galactosyl-α-D-galactosyl-α-D-glucosy-β-D-fructose (a stachyose derivative).

The preferred polysaccharides comprise at least one simple sugar linkage selected from the group consisting of 5-C-hydroxymethylaldohexose; 1,6-anhydro-5-C-hydroxymethyl-β-D-aldohexopyranose; 1,6-anhydro-5-C-hydroxymethyl-β-L-aldohexopyranose; 5-C-hydroxymethylaldohexosyl polyol derivatives; alkyl 5-C-hydroxymethylaldohexoside, 5-C-hydroxymethylketohexose, 5-C-hydroxylmethylketohexosyl polyol derivatives and alkyl 5-C-hydroxymethylketohexoside where the alkyl is selected from the group consisting of methyl, ethyl, propyl and isopropyl. Finally, the most preferred polysaccharide embodiment is an arabinogalactan derivative wherein at least one D-galactosyl component is replaced with a 5-C-hydroxymethyl-α-L-arabinopyranosyl group.

USES OF THE NOVEL COMPOUNDS

The novel compounds described above and their alditols (i.e., hexitols) provide sugar-like functionality (i.e., degree of hydration, viscosity, color, texture, odor and bulk) with significantly reduced calories (often none) compared with conventional caloric sugars (e.g., sucrose, fructose, glucose, etc.). Several of these compounds also exhibit some sweetness (about 30% sucrose). In addition, these novel compounds exhibit sugar-like characteristics when used in a wide range of food compositions. These novel compounds and their alditols are particularly effective in producing low calorie food compositions.

A. FOOD COMPOSITIONS

Novel food compositions of the present invention contain from about 1% to about 99% of any of the above-mentioned compounds. Preferred embodiments of these food compositions include baked goods, fruit drinks/mixes, frozen foods, candies, carbonated beverages, milk drinks/mixes, gelatins, puddings, fillings, breakfast cereals, breakfast bars, sauces, jams, jellies, whipped toppings, tablets, syrups, orally administered medicines, spreads, chewing gums and chocolates. The most preferred food compositions are baked goods.

Food compositions with reduced caloric value are often prepared by directly substituting one of the above-mentioned compounds for sucrose in a typical food formulation. Due to the natural variation of natural raw materials, the ratio of ingredients may need to be varied by a skilled food technologist.

Just as adjustments are made in recipes and formulations for the different properties of sucrose and fructose or dextrose, adjustments for the different properties of these sugar derivatives must be made. These changes are within the skill of one in the art.

The following is by way of example a partial list of food compositions which can be made with these sugar derivatives: cakes, cookies, brownies, other sweet snacks, icings, frostings, pie fillings, puddings, creams, hard and soft candies, chocolates, crackers, snacks made from potatoes, corn, wheat and other grains, sauces gravies, yogurt, breadings, breads (some sugar must be added to make the yeast work), rolls, muffins, doughnuts and sweet rolls.

B. Sugar Substitutes

Several of the novel compounds and/or their alditols exhibit a low sweetness intensity relative to sucrose. By using these compounds as bulking compounds in combination with a known sweetening compound of higher sweetening intensity, a composition which provides sucrose-like characteristics is produced (i.e., a sugar substitute). These sugar substitute compositions comprise from about 1% to about 99.99% of one or a mixture of the above-mentioned novel compounds and/or their alditols and from about 0.01% to about 99% of a sweetening compound. Preferred novel compound components include 5-C-hydroxymethylaldohexose; 1,6-ahydro-5-C-hydroxymethyl-β-D-aldohexopyranose; 1,6-anhydro-5-C-hydroxymethyl-β-L-aldohexopyranose; 5-C-hydroxymethylaldohexosyl polyol derivatives; alkyl 5-C-hydroxymethylaldohexoside, where the alkyl is selected from the group consisting of methyl, ethyl, propyl and isopropyl; 5-C-hydroxymethylaldohexitols; di-, tri-, oligo- or polysaccharides comprised from the above-mentioned simple sugars and mixtures of these compounds.

The most preferred novel compounds include 5-C-hydroxymethyl-L-arabino-hexose; 5-C-hydroxymethyl-D-xylo-hexose; 5-C-hydroxymethyl-D-lyxo-hexose 1,6-anhydro-5-C-hydroxymethyl-β-L-altropyranose, 1,6-anhydro-5-C-hydroxymethyl-β-L-idopyranose; 1,6-anhydro-5-C-hydroxymethyl-β-L-gulopyranose;
Methyl 5-C-hydromethyl-arabino-hexoside; ethyl 5-C-hydroxymethyl-L-arabino-hexoside; 5-C-hydroxymethyl-L-arabino-hexosyl glycerol; 5-C-hydroxymethyl-α-D-xylo-hexopyranosyl-β-D-fructofuranoside; 5-C-hydroxymethyl-α-L-arabino-hexopyranosyl-(1→4)-D-galactopyranose; 5-C-hydroxymethyl-α-L-arabino-hexopyranosyl-(1→6)-D-galactopyranose; 5-C-hydroxymethyl-α-L-arabino-hexopyranosyl-α-D-glucosyl-D-fructose; 5-C-hydroxymethyl-α-L-arabino-hexopyranosyl-D-galactosyl-α-D-glucosyl-α-D-fructose; 5-C-hydroxymethyl-α-L-arabino-hexopyranosyl-D-glucitol; arabinogalactan derivatives whereby at least one galactosyl group is converted to a 5-C-hydroxymethyl derivative; and mixtures thereof.

These sugar substitutes may further comprise from about 1% to about 99% of conventional bulking compound. Preferred conventional bulking compounds include polydextrose, arabinogalactan, gum arabic, gum tragacanth, locust bean gum, carrageenan, guar gum, agarose, or mixtures thereof.

Preferred sweetening compounds include sucrose, glucose, fructose, lactitol, maltitol, sorbitol, alitam, sucralose, acesulfame, aspartame, cyclamates, saccharin and mixtures of these compounds.

C. COMBINATIONS WITH ZERO OR LOW CALORIE FATS

The novel compounds or their polyols can also be used in combination with a polyol polyester compound to provide a food composition with nearly no caloric value. Low calorie fat containing food compositions of the present invention are those wherein from about 10% to about 100% of the total fat in the food composition consists of a polyol polyester compound, and which comprise from about 1% to about 99% of one or a mixture of the above-mentioned novel compounds or their alditols. Preferred polyol polyester compounds include glucose tetraoleate, glucose tetrastearate, glucose tetraester of soybean oil fatty acid, mannose tetraester of tallow fatty acid, galactose tetraester of olive oil fatty acid, arabinose tetraester of cottonseed oil fatty acid, xylose tetralinoleate, galactose pentastearate, sorbitol tetraoleate, sorbitol hexaester of olive oil fatty acid, xylitol pentapalmitate, xylitol tetraester of substantially completely hydrogenated cottonseed oil fatty acid, sucrose tetrastearate, sucrose pentastearate, sucrose hexaoleate, sucrose octaester of substantially completely hydrogenated soybean oil fatty acid, sucrose octaester of peanut oil fatty acid, erythritol tetraester of olive oil fatty acid, erythritol tetraoleate xylitol pentaoleate, sorbitol hexaoleate, sucrose octaoleate, sucrose octaester of soybean oil fatty acid and mixtures of these compounds. Sucrose fatty acid polyesters, wherein at least about 60% of the polyesters are octaester are particularly preferred.

The very low degree of metabolism of the novel carbohydrate compounds serves to reduce dental caries and to extend the shelf life of food compositions containing these compounds. Food compositions containing these compounds are particularly useful in the treatment of diabetes. Drug compositions containing the above-mentioned compounds are particularly efficacious where a low calorie level is critical or where conventional sugars are deleterious.

It has recently been found (concurrently-filed U.S. patent application Ser. No. 190,485, filed May 5, 1988 Mazur, Hiler, Stipp and Kluesener) that the 5-C-hydroxy methylation of D-aldohexose-based compounds can be accomplished by a process which comprises an enzymic oxidation reaction followed by a condensation reaction with formaldehyde.

The preparation of the foregoing compounds and their use in food compositions and sugar substitutes is described in the following examples:

EXAMPLE I

Preparation of methyl 5-C-hydroxymethyl-α-L-arabino-hexopyranoside from methyl β-D-galactoside.

1. Oxidation of Methyl β-D-Galactopyranoside with Galactose Oxidase

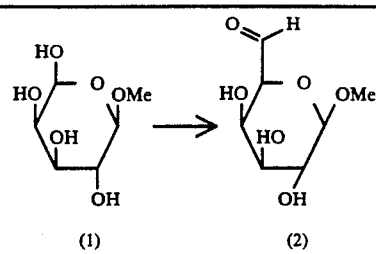

| Reagents | MW | Moles | Amount |
|---|---|---|---|
| methyl β-D-galactopyranoside Sigma Chemical Co., (No. M-6757) | 194.18 | 0.103 | 20.0 g |
| Phosphate Buffer, 100 mM | — | — | 412.0 ml |
| Catalase, 16900 units/mg Sigma Chemical Co., (No. C-40) | — | — | 7.5 mg |
| Galactose Oxidase | — | — | 9000 units |

The reaction is conducted in a one liter vessel equipped with an aerator and a gentle stirrer. Sterile conditions are used to prevent enzyme deactivation by microbial contamination. The reaction is run at 4° C. to minimize deactivation of galactose oxidase.

Methyl β-D-galactopyranoside (1) is dissolved in the aerated phosphate buffer. The volume flow of air discharged by the aerator is regulated to produce an oxygen saturated solution while preventing foaming of the solution. At 4° C., the galactose oxidase and catalase are added and this solution is aerated for 20 hours.

The enzymes are removed from the product solution by ultrafiltration using a 10,000 MWCO membrane (Diaflo 13242, manufactured by Amicon). The resulting filtrate contains the oxidation product, methyl β-D-galacto-hexodialdo-1,5-pyranoside (2).

2. Condensation of Oxidation Product With Formaldehyde to Methyl 5-C-Hydroxymethyl-α-L-arabino-hexopyranoside (3)

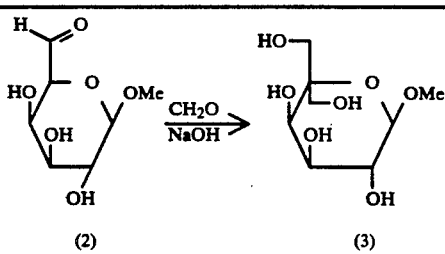

| Reagents | Amount |
|---|---|
| filtrate solution containing the oxidation product methyl β X⁻ D-galacto-hexodialdo-1,5-pyranoside from step 1. | 400 ml |
| 37% formaldehyde solution (aqueous) | 400 ml |
| 50% sodium hydroxide solution (aqueous) | 144 ml |

The filtrate solution from step 1 and the formaldehyde solution are combined in a one liter vessel. The sodium hydroxide solution is added to the filtrate/formaldehyde solution over a period of 1 hour while the solution temperature is maintained between 20° C. and 25° C. with an ice-water bath. After the exothermic reaction has ceased, the ice-water bath is removed and the reaction mixture is stirred at room temperature for 16 hours. The reaction mixture is heated to 55° C. and deionized using ion exchange columns: first Amberlite IR-120(H+), then Amberlite IRA-400(OH−), both packings manufactured by Rohm & Haas. Finally, the deionized solution of the product is eluted through an Amberlite IRA-400 (HSO3−) ion exchange column to remove remaining formaldehyde. Slow room temperature evaporation to dryness, followed by drying of the residue at room temperature under vacuum overnight produces 18.5 g (80%) of (3).

EXAMPLE II

Preparation of
1,6-anhydro-5-C-hydroxymethyl-β-L-altropyranose (4)

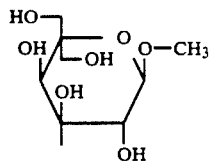
(3)

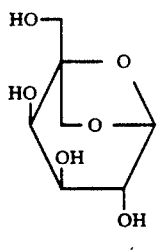
(4)

Methyl 5-C-hydroxymethyl-α-L-arabino-hexopyranose (3) (59.0 g, 0.263 moles) is dissolved in 0.70M sulfuric acid (260 ml), and stirred at 100° C. for 90 minutes. The solution is cooled to room temperature and neutralized using an ion exchange resin (Amberlite IRA-400 (OH−). The resin is filtered off, and the filtrate is refluxed for 15 minutes with activated carbon (4.0 g). Carbon is removed with a glass fiber filter, and the filtrate is evaporated to dryness with ethanol. The white waxy residue is refluxed for 15 minutes with methanol (50 ml). The solution is stored overnight at 0° C. The product is filtered to yield 20.0 g (39.6%) of 1,6-anhydro-5-C-hydroxymethyl-β-L-altropyranose (4).

M.P.=166.5° C.-168.5° C.

$[\alpha]_D^{23}$=+145.1 (C 7.2 in water).

Preparation of
5-C-hydroxymethyl-L-arabino-hexofuranose (8)

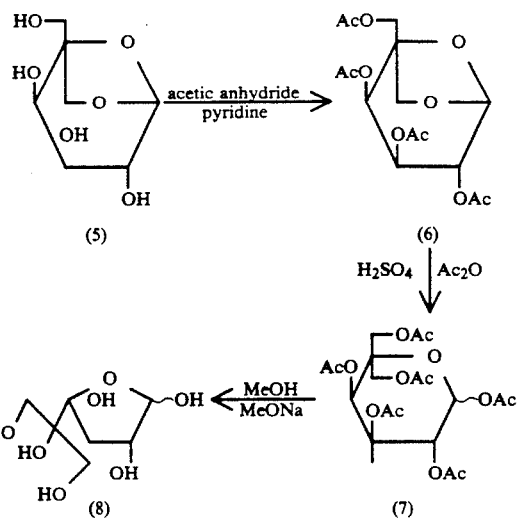

1. Preparation of
5-(acetoxymethyl)-1,2,3,4,6-penta-O-acetyl-L-arabino-hexopyranose (7)

A solution of crude 1,6-anhydro-5-C-hydroxymethyl-β-L-altropyranose (5) (10.0 g, 52 mmol) in a mixture of acetic anhydride (100 ml) and pyridine (100 ml) is stirred at room temperature for 3 hours. The reaction mixture is poured into ice water (300 ml), the product is extracted with methylene chloride (300 ml). The organic phase is washed with 1M HCl (3×400 ml), sodium bicarbonate (300 ml) and water (300 ml).

Evaporation of solvent produces crude 19.0 g of 5-C-acetoxymethyl-1,6-anhydro-2,3,4-tri-O-acetyl-β-L-altropyranose (6) which, without further purification, is dissolved in acetic anhydride (300 ml) and the solution is cooled to 0° C. While maintaining this temperature, sulfuric acid (30.0 g) is slowly added. When the addition is complete, the ice bath is removed and the solution is stirred at ambient temperature for 2 hours. At that time, TLC (Analtech GF plates, toluene:acetone 2:1) shows a single major product with a small amount of more polar impurities. An excess of acetic anhydride is destroyed by slow addition of water (45 ml) with cooling at temperature below 30° C. The resulting solution is partitioned between methylene chloride (300 ml) and aqueous sodium bicarbonate (300 ml), the organic phase is washed repeatedly with sodium bicarbonate (3×300 ml) and water (300 ml). Evaporation of the solvent gives 17.0 g (70% yield) of (7).

$[\alpha]_D^{26.2}$=+39.5° (C8.3 in CHCl3)

Anal. calc. for $C_{19}H_{26}O_{13}$: C, 49.35; H, 5.67. Found: C, 49.16; H, 5.60.

2. Preparation of
5-C-Hydroxymethyl-L-arabino-hexofuranose (8)

A solution of 5-C-(acetoxymethyl)-1,2,3,4,6-penta-O-acetyl-L-arabino-hexopyranose (7) (4.0 g, 8.7 mmol) in 0.05M methanolic sodium methoxide (50.0 ml) is stirred at room temperature for 2 hours. The reaction mixture is deionized with Amberlite IR-120 (H+) and evaporated to oily residue. Purification on a silica column with chloroform:methanol (4:1) followed by chloroform:methanol (3:2) gives 0.5 g (27%) of (8).

EXAMPLE IV

Preparation of ethyl 5-C-hydroxymethyl-L-arabino-hexofuranoside (9) and ethyl-5-C-hydroxymethyl-L-arabino-hexopyranoside (10)

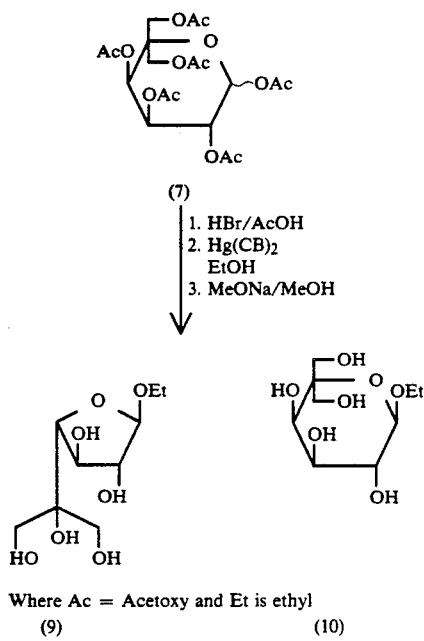

Where Ac = Acetoxy and Et is ethyl
(9)        (10)

A solution of hydrogen bromide in acetic acid, prepared by slow addition of acetic anhydride (30 ml) to 48% HBr (8 ml) at 15°–30° C., is added to 5-acetoxymethyl-1,2,3,4,6-penta-O-acetyl-L-galactopyranose (7) (2.5 g, 5.1 mmol) and is stirred for 2.5 hours at room temperature. The reaction mixture is then partitioned between ice-cold water and methylene chloride. The organic layer is deacidified with a saturated sodium bicarbonate solution and washed with cold water. After drying with anhydrous sodium sulfate, the solvent is evaporated at 25°–30° C. to a brown residue which is further dried under high vacuum for 30 minutes. This residue, without further purification, is treated with mercuric cyanide (0.6 g, 2.3 mmol) in absolute ethanol (40 ml) for 2 hours at 50° C. After evaporation of the solvent, the residue is dissolved in chloroform, washed with an aqueous sodium bicarbonate solution. The chloroform solution is dried with anhydrous sodium sulfate and evaporated to dryness. The residue is deacetylated with 0.05M MeONa/MeOH solution, giving a mixture of two major products which are separated on a silica column with chloroform:methanol (4:1). The faster moving compound is ethyl 5-C-hydroxymethyl-L-arabino-hexofuranoside (9) 0.25 g (20.5%) and the slower moving product is methyl 5-C-hydroxymethyl-L-arabino-hexopyranoside (10) 0.1 g (8.2%).

EXAMPLE V

Preparation of methyl 5-C-hydroxymethyl-α-D-xylo-hexopyranoside (13)

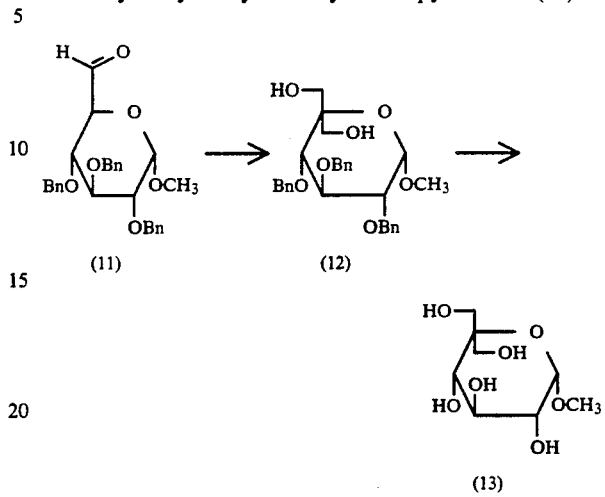

where Bn=benzyl. 2,3,4-tri-o-benzyl-methyl-α-D-gluco-hexodialdo-1,5-pyranoside (11) (12.0 g, 0.025 moles) is dissolved in 1,4 dioxane (320 ml) and added to a solution of 1M NaOH (130 ml) and 37% CH$_2$O (130 ml). This solution is stirred overnight (20 hours), neutralized with formic acid and evaporated. The remaining oily residue is dissolved in CH$_2$Cl$_2$ (50 ml), washed with 2×50 ml H$_2$O, dried with NaSO$_4$, and evaporated. The product is purified on 100 ml of silica gel with an ethyl acetate:hexane solvent system, 45:55 (vol/vol). Two fractions are collected. The second fraction is methyl 5-C-hydroxymethyl-2,3,4-tri-o-benzyl-α-D-xylo-hexopyranoside (12) (5.75 g (45%)). The compound (12) (5.5 g, 0.0112 moles) is dissolved in 50% methanol (50 ml), acetic acid (15 ml), and treated with palladium hydroxide (6.0 g), and hydrogen gas (P=1 Atm.), for 20 hours. The solution is then filtered, deionized using ion exchange resin Amberlite IRA-400 (OH−) (15 ml), and evaporated. The remaining oil is methyl 5-C-hydroxymethyl-α-D-xylo-hexopyranoside (2.4 g, 98%) (13).

EXAMPLE VI

Preparation of 1,6-anhydro-5-C-hydroxymethyl-β-L-idopyranoside (14)

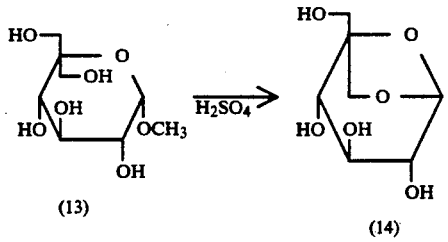

Methyl-5-C-hydroxymethyl-α-D-xylo-hexopyranoside (13) (100 mg., 0.00045 moles) is treated with 0.375M sulfuric acid (0.75 moles). The solution is kept at 100° C. for 90 minutes, cooled and neutralized with ion exchange resin Amberlite IRA-400 (OH−) (15 ml). The solution is filtered and evaporated to give 50 mg of 1,6-anhydro-5-C-hydroxymethyl-β-L-idopyranoside (14) (65%).

EXAMPLE VII

Preparation of 5-C-hydroxymethyl-D-lyxo-hexopyranose (16) and 1,6-anhydro-5-C-hydroxymethyl-β-L-gulose (17).

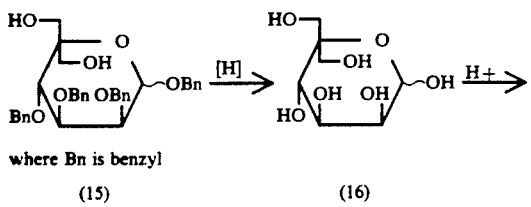

where Bn is benzyl

(15)    (16)

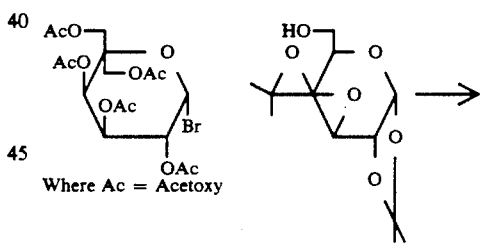

(17)

1,2,3,4-tetra-D-benzyl-5-C-hydroxymethyl-L-lyxo-hexopyranose (15) (9 g, 0.0158 mole) is dissolved in methanol (50 ml) and added to water (50 ml) containing palladium hydroxide on carbon (9 g, Aldrich 21,291-1). The mixture is hydrogenated under atmospheric pressure for 16 hours. After a careful evacuation of hydrogen and flushing with nitrogen, the reaction mixture is heated on a steam bath for 15 min. The catalyst is removed by filtration. Evaporation of the filtrate produces 3.1 g of a crude mixture of α and β isomers of 5-C-hydroxymethyl-L-lyxo-hexopyranose (16). This product (2.5 g,16) is dissolved in 0.5M sulfuric acid and stirred at 100° C. for 90 min. After cooling to room temperature, the solution is neutralized with IRA-400(OH), treated with charcoal (0.5 g), filtered and evaporated. TLC examination of the solution, done on the Whatman KF plates with acetonitrile/water mixture 8:2, reveals the presence of 1,6-anhydro-5-C-hydroxymethyl-β-L-gulose (17) as well as 5-C-hydroxymethyl-L-lyxohexopyranose (16). 1,6-anhydro-5-C-hydroxymethyl-β-L-gulose (17), is separated using silica column (Matrex silica 60 A, Amicon Corp.) and eluent chloroform/methanol 8:2. Yield of the product (17) is 0.9 g.

EXAMPLE VIII

Preparation of 5-C-hydroxymethyl-α-L-arabino-hexopyranosyl (1→6)-D-galactopyranose and -galactofuranose.

1. Preparation of 5-C-acetoxymethyl-2,3,4,6-tetra-O-acetyl-α-L-arabino-hexopyranosyl bromide (18)

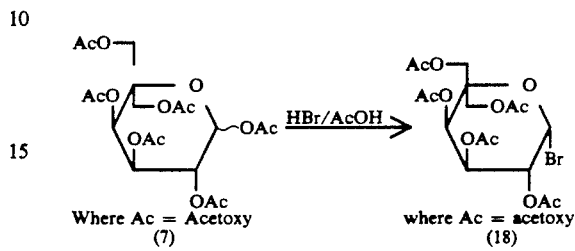

Glacial acetic acid (60 ml) is saturated with dry gaseous HBr for 30 minutes at 18°-20° C. This solution is mixed with 5-C-acetoxymethyl-1,2,3,4,6-penta-O-acetyl-L-arabino-hexopyranose (7) (6.0 g, 0.013 ml) and is stirred at an ambient temperature for 3.5 hours. Workup of the reaction mixture involves: dilution with methylene chloride (150 ml), washing with ice-water, sat. sodium bicarbonate solution, and water again. After drying the methylene chloride solution with sodium sulfate (anhydrous), evaporation of the solvent produces crude 5-C-acetoxymethyl-2,3,4,6-tetra-O-acetyl-α-L-arabino-hexopyranosyl bromide (18) (3 g) which is dried under high vacuum for 30 minutes and is used for the glycosidation reactions without further purification.

2. Preparation of O-(5-C-hydroxymethyl-α-L-arabino-hexopyranosyl)(1→6)-1,2:3,4-diisopropylidene-α-D-galactopyranose (20)

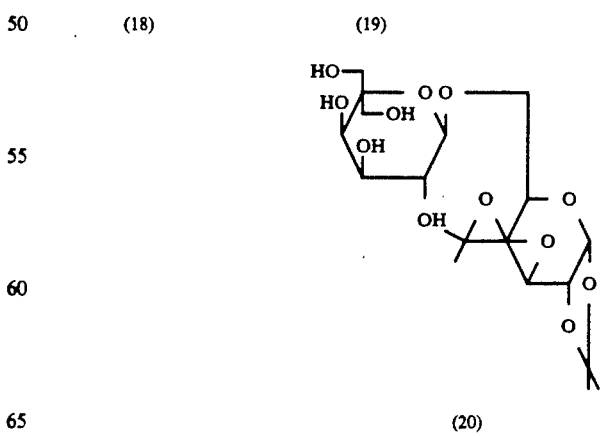

Crude 5-C-acetoxymethyl-2,3,4,6-tetra-O-acetyl-L-arabino-hexopyranosyl bromide from step 1 (18) (3.0 g), 1,2:3,4-diisopropylidene-α-D-galactopyranose (19) (5.25 g, 20 mmol), mercuric cyanide (2.0 g, 8 mmol) in dry dichloroethane (120 ml) are reacted overnight at 40° C.

After evaporation of the solvent, the residue is dissolved in chloroform, and washed with an aqueous sodium bicarbonate solution (saturated). The chloroform solution is dried with anhydrous sodium sulfate and evaporated to dryness. The residue is deacetylated with 0.05M MeONa/MeOH solution. Yield 1.75 g O-(5-C-hydroxymethyl-α-L-arabino-hexopyranosyl) (1→6)-1,2:3,4-diisopropylidene-α-D-galactopyranose (20).

3. Preparation of O-(5-C-Hydroxymethyl-α-L-arabino-hexopyranosyl (1→6)-D-galactopyranose (21) and O-(5-C-hydroxymethyl-α-L-arabino-hexopyranosyl (1→6)-D-galactofuranose (22)

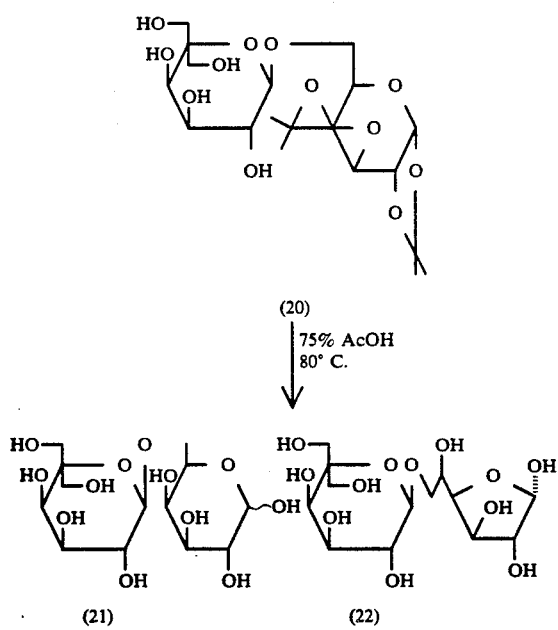

O-(5-C-hydroxymethyl-α-L-arabino-hexopyranosyl)-(1→6)-1,2:3,4-diisopropylidene-α-galactopyranose (20) (1.75 g) is stirred in acetic acid 75% (30 ml) at 80° C. for 3 hours. The slightly yellow solution is treated with charcoal and cooled to room temperature. Filtration and evaporation of solvent is followed by crystallization of the residue from acetic acid gives 0.7 g (50%) of the mixture of (21) and (22).

EXAMPLE IX

5-C-hydroxymethylation of lactitol

1. Enzymic Oxidation of Lactitol

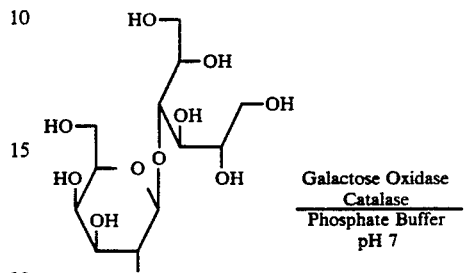

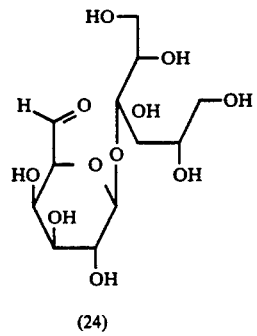

| Reagent | Amount |
| --- | --- |
| Lactitol (23) (manufactured by CCA BioChem) | 20.0 g |
| Phosphate Buffer, 100 mM, pH 7 | 232.0 ml |
| Catalase (Sigma), 16900 u/mg | 7.00 mg |
| Galactose Oxidase | 9000 units |

The reaction is conducted in a vessel equipped with a gentle stirrer and an aerator. Sterile conditions are used to prevent enzyme deactivation by microbial contamination. The reaction is run at 4° C. to minimize deactivation of galactose oxidase.

Lactitol (23) is dissolved in the aerated phosphate buffer. At 4° C., the galactose oxidase and catalase are added and this solution is aerated to maintain oxygen saturation for 20 hours.

The enzymes are removed from the product solution by ultrafiltration using a 10,000 MWCO membrane (Diaflo 13242, manufactured by Amicon). The resulting filtrate contains the oxidation product (24).

2. Condensation of Oxidation Product With Formaldehyde

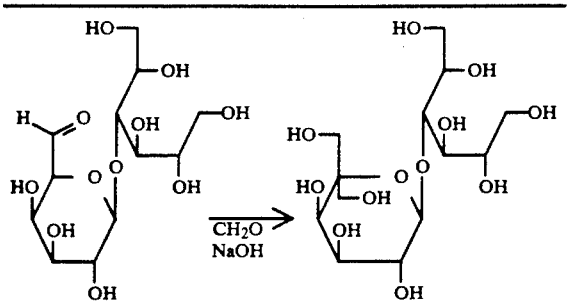

(24)           (25)

| Reagents | Amount |
| --- | --- |
| filtrate solution containing the oxidation product (24) from step 1 | 400 ml |
| 37% formaldehyde solution | 400 ml |
| 50% sodium hydroxide solution (aqueous) | 144 ml |

The filtrate solution and the formaldehyde solution are combined in a one liter vessel. The sodium hydroxide solution is added to filtrate/formaldehyde solution over a period of 1 hour while the solution temperature is maintained between 20° C. and 25° C. with an ice-water bath. After the exothermic reaction has ceased, the ice-water bath is removed and the reaction mixture is stirred at room temperature for 16 hours. The reaction mixture is heated to 55° C. and deionized using ion exchanger columns: first Amberlite IR-120 (H+), then Amberlite IRA-400 (OH−). Finally, the deionized solution of the product is eluted through a column with Amberlite IRA-400 ($HSO_3-$) in order to remove remaining formaldehyde. Evaporation to dryness followed by drying the residue at room temperature under vacuum overnight produces 11.9 g (55% yield) of 5-C-hydroxymethyl-α-L-arabino-hexopyranosyl-D-glucitol (25).

The 5-C-hydroxymethylation of galactosyl groups described above is readily adapted by one skilled in the art to other di-, tri- and oligosaccharides containing at least one galactosyl group. Applicable starting compounds for this type of 5-C-hydroxymethylation are raffinose (i.e., O-α-D-galacto pyranosyl-(1→6)-α-D-glucopyranosyl-β-D-fructofuranoside), stachyose (i.e., O-α-D-galactopyranosyl-(1→6)-O-α-D-galactopyranosyl-(1→6)-α-D-glucopyranosyl-α-D-fructofuranoside), arabino- galactan and D-galactopyranosyl glycerols.

EXAMPLE X

Preparation of brownies containing 5-C-hydroxymethyl-α-L-arabino-hexopyronosyl-D-glucitol.

| Ingredient | Amount (gms) |
| --- | --- |
| 5-C-hydroxymethyl-α-L-arabino-hexopyranosyl-D-glucitol (as prepared in Example IX) | 309.8 g |
| Flour | 152 g |
| Vegetable shortening | 50 g |
| Cocoa | 35.3 g |
| Starch | 11.7 g |
| Conventional additives (flavors and a small amount of baking soda) | 6.2 g |
| Eggs | 50 g |
| Oil | 63 g |
| Water | 80 g |

The ingredients are stirred with a large spoon until well blended (about 50 strokes or 1 minute) to form a batter. The batter is poured into a lightly greased 13"×9"×2" pan, and then baked at 350° F. for about 26.5 minutes to produce the finished brownies.

EXAMPLE XI

Preparation of cookies containing 1,6-anhydro-5-C-hydroxymethyl-β-L-altropyranose.

| Ingredients | Amounts (gms) |
| --- | --- |
| 1,6-anhydro-5-C-hydroxymethyl-β-L-altropyranose (as prepared in Example II) | 176 |
| Table Sugar (i.e., sucrose) | 176 |
| Flour | 328 |
| Shortening | 196 |
| Egg | 96 |
| Water | 20 |
| Conventional additives (flavors and a small amount of baking soda) | 8 |

The ingredients are combined and the resulting dough is kneaded until uniform. Dough balls (10–13 gm) are individually placed on a lightly greased cookie tray and then baked at 350° F. for 7–8 minutes to produce finished cookies.

EXAMPLE XII

Preparation of a white cake containing 5-C-hydroxymethyl-α-D-xylo-hexopyranoside

| Ingredients | Amount (gms) |
| --- | --- |
| 5-C-hydroxymethyl-α-D-xylo-hexopyranoside (as prepared in Example V) | 133 |
| Cake flour | 107 |
| Erythritol tetraester of olive oil fatty acid (a polyol polyester used used as a shortening) | 47.5 |
| Double-acting baking powder | 6.7 |
| Milk | 130 |
| Egg whites | 60 |
| Vanilla | 2.5 |

The ingredients are stirred with an electric mixer to form a uniform batter. The batter is poured into a lightly greased 13"×9"×2" pan, and then baked at 350° F. for 40 minutes to produce the finished white cake. This cake looks and tastes like a conventional white cake, but has nearly no caloric value.

EXAMPLE XIII

Sugar Substitute Compositions

The following list exemplifies sugar substitute formulations which provide sweetness and bulk similar to sucrose.

(a) 0.4% aspartame and 99.6% methyl 5-C-hydroxymethyl-α-L-arabino-hexopyranose (b) 0.5% aspartame and 99.5% 1,6-anhydro-5-C-hydroxymethyl-β-L-altropyranose (c) 0.3% saccharin and 99.7% 5-C-hydroxymethyl-β-D-xylohexopyranose (d) 49.5% 5-C-hydroxymethyl-$\beta$-D-xylo-pyranosyl-$\beta$-D-fructofuranoside, 49.4% sucrose, and 0.1% aspartame.

(e) 49.5% 5-C-hydroxymethyl-$\alpha$-L-arabino-hexopyranosyl-D-glucitol, 49.4% polydextrose, and 0.1% aspartame.

EXAMPLE XIV

Methyl 1-O-benzyl-$\alpha$-D-fructofuranoside (26) and methyl 1-O-benzyl-D-fructofuranoside (27)

2,3:4,5-diisopyropylidene-$\alpha$-fructopyranose (15.0 g, 57.6 mmole) is dissolved in dry dimethylformamide (250) containing benzyl chloride (11.05 ml, 96 mmole). When the exothermic reaction ceases, the mixture is stirred at room temperature for 1.5 hours. Any excess hydride is decomposed with methanol, and the pH is adjusted to neutral with acetic acid. Filtration and evaporation of solvents produces 22 g of a crude oil containing 1-O-benzyl-2,3:4,5-diisopropylidene=$\alpha$-D-fructopyranose ($R_F$=0.56, Analtech GF plates, toluene:acetone 4:1). This crude mixture is dissolved in 1% iodine solution in methanol (200 ml) and is refluxed for 24 hours. Sodium bisulfate is added to reduce the iodine and the mixture is filtered. The filtrate is evaporated and the products are separated on a silica column with chloroform:methanol 20:1. The combined fractions give 11.0 g (70%) of a mixture containing a ratio of (26) and (27) to (4C) approx. 2:1. Further chromatography of this product on silica column with chloroform: methanol 6:1 produces 6.55 g (40%) of (26) and (27), combined.

EXAMPLE XV

Methyl 1,3,4-tri-O-benzyl-$\alpha$-D-fructofuranoside (28), and methyl 1,3,4-tri-O-benzyl-$\beta$-D-fructofuranoside (29)

A mixture of methyl 1-O-benzyl-($\alpha$+$\beta$)-fructofuranosides, (26) and (27) (10.0 g, 35 mmole), triphenylmethyl chloride (12.2 g, 44 mmole), pyridine (90 ml), 4-dimethylaminopyridine (0.1 g) is stirred at 40° C. for 24 hours. The mixture is poured into ice water (400 ml), and the product is extracted with ethyl acetate (500 ml). The organic layer is washed with 1N HCl (2×400 1), saturated sodium bicarbonate, and with water again (400 ml). The solvent is evaporated and the residue was dried under high vacuum in the presence of $P_2O_5$ overnight. The resulting orange oil, containing methyl 1,3,4-tri-O-benzyl-6-triphenylmethyl-($\alpha$+$\beta$-fructofuranosides (29), ($R_F$=0.25, analtech GF plates, toluene:acetone 4:1), is benzylated in dry dimethylformamide (380 ml) with benzyl chloride (20.1 ml, 175 mmole) and 60% sodium hydride (7.0 g, 175 mmole) for 1.5 hours at room temperature. Excess hydride is decomposed with methanol. The pH is adjusted to neutral with acetic acid and the solvent is evaporated. The crude product, a mixture of methyl 1,3,4-tri-O-benzyl-6-triphenylmethyl-($\alpha$+$\beta$)-fructofuranosides (30), ($R_F$ 0.11 and 0.16, hexane:ethyl acetate 20:1), is dissolved in a mixture of methanol (200 ml), 1,4-dioxane (100 ml) and trifluoracetic acid (75 ml), and is refluxed for 5 hours. The acid is neutralized with $Na_2CO_3$, and the solid material is filtered. The filtrate is evaporated to an oily residue which is dissolved in ethyl ether, washed with water, and is evaporated again. The residue, containing three major compounds, is purified on a silica column (2.5 1) using toluene:acetone 5:1 mixture for elution. Two main, faster moving products were collected giving 13.5 g (83%) of a mixture of (28) and (29).

EXAMPLE XVI

Methyl 5-C-hydroxymethyl-1,3,4-tri-O-benzyl-$\beta$-D-erythrohexulofuranoside (31) and Methyl 5-C-hydroxymethyl-1,3,4-tri-O-benzyl-$\alpha$-D-erthro-hexulofuranoside (32)

An oxidizing mixture is made by a careful addition at $-70°$ C. of a dry solution of dimethylsulfoxide (4.98 ml, 70 mmole) and methylene chloride (30 ml) into a solution of oxalyl chloride (3.04 ml, 35 mmole) in dry methylene chloride (160 ml), and stirring the resulting solution for 10 min. While maintaining the temperature $-70°$ C., a solution of methyl 1,3,4-tri-O-benzyl ($\alpha$+$\beta$)-fructofuranosides (28, 29) in dry methylene chloride (60 ml) is added over a period of 10 min and stirring is continued for an additional 45 min. After subsequent addition of dry triethylamine (20.2 ml, 145 mmole) the reaction mixture is allowed to warm to room temperature. The product (aldehyde) solution is washed with water (50 ml), 1N HCl (200 ml), saturated sodium bicarbonate and water (200 ml) again. Evaporation of the solvent in vacuo produces a residue, containing methyl 1,3,4-tri-O-benzyl-($\alpha$+$\beta$)-D-fructofuranose-6-guloside (33), which is dissolved in 1,4-dioxane (250 ml). The hydroxymethylation reaction is initiated by adding to this solution 37% formaldehyde (44 ml) and 1M sodium hydroxide (44 ml). The mixture is stirred at room temperature for 20 hours, neutralized with 1N HCl and evaporated to dryness. The residue is fractionated on a silica column using a mixture of toluene:acetone 10:1. Yields: $\alpha$=isomer (32) 2.25 g (15.7%), $\beta$-isomer (31) 1.75 g (12.2%).

EXAMPLE XVII

Methyl 5-C-hydroxymethyl-$\alpha$-D-erythro-hexulofuranoside (34)

5-C-hydroxymethyl-1,3,4-tri-O-benzyl-$\alpha$-D-erythrohexulofuranoside (32) (2.25 g, 4.5 mmole) is hydrogenated (atmospheric pressure, room temperature) in methanol in the presence of 20% palladium hydroxide on charcoal (3.0 g), for 20 hours. The reaction mixture is filtered through Celite. The cake is washed with hot water, and the filtrate is evaporated to dryness producing quantitative yield, 1.15 g. of (34).

Methyl 5-C-hydroxymethyl-$\alpha$-D-erythro-hexulofuranoside (35)

Methyl 5-C-hydroxymethyl-1,3,4-tri-O-benzyl-$\beta$-D-erythrohexulofuranoside (31) (1.75 g, 2.5 mmole) is exposed to the procedure identical to that for making the $\alpha$-isomer. Yield of (35), 0.8 g (100%).

What is claimed is:

1. A 5-C-hydroxymethyl hexose compound wherein one or more of the hydroxyl groups is esterified with a carboxylic acid.

2. A compound according to claim 1 wherein said carboxylic acid is an alkyl carboxylic acid.

3. A compound according to claim 2 wherein 3 or more hydroxyl groups are esterified.

4. A compound according to claim 3 wherein said 5-C-hydroxymethyl hexose is covalently bonded through a glycosidic linkage to a monosaccharide or a disaccharide.

5. A compound according to claim 4 wherein 4 or more of the hydroxyl groups are esterified.

6. A 5-C-hydroxymethyl hexose compound wherein one or more of the hydroxyl groups is converted to an ether moiety.

7. A compound according to claim 6 wherein said ether moiety comprises an alkyl group.

8. A compound according to claim 6 wherein said 5-C-hydroxymethyl compound is covalently bonded through a glycosidic linkage to a monosaccharide or a disaccharide.

9. A compound according to claim 2 wherein said carboxylic acid is a lower alkyl carboxylic acid.

10. A compound according to claim 1 wherein said carboxylic acid is an aryl carboxylic acid.

11. A compound according to claim 10 wherein said carboxylic acid is benzyl carboxylic acid.

12. A compound according to claim 7 wherein said ether moiety is a lower alkyl group.

* * * * *